US00PP28580P3

(12) United States Plant Patent
Yang et al.

(10) Patent No.: US PP28,580 P3
(45) Date of Patent: Oct. 31, 2017

(54) KIWIFRUIT PLANT NAMED 'YANG'S GOLDEN RED NO. 1'

(50) Latin Name: *Actinidia chinensis*
Varietal Denomination: Yang's Golden Red No. 1

(71) Applicants: Shengmou Yang, Yangzhou (CN); Xiaoqin Jiang, Yangzhou (CN); Ying Lv, Yangzhou (CN); Jian Yang, Yangzhou (CN)

(72) Inventors: Shengmou Yang, Yangzhou (CN); Xiaoqin Jiang, Yangzhou (CN); Ying Lv, Yangzhou (CN); Jian Yang, Yangzhou (CN)

( * ) Notice: Subject to any disclaimer, the term of this patent is extended or adjusted under 35 U.S.C. 154(b) by 182 days.

(21) Appl. No.: 14/756,546

(22) Filed: Sep. 16, 2015

(65) Prior Publication Data
US 2017/0079172 P1 Mar. 16, 2017

(51) Int. Cl.
*A01H 5/08* (2006.01)

(52) U.S. Cl.
USPC ..... Plt./156

(58) Field of Classification Search
USPC ..... Plt./156
CPC ..... A01H 5/08
See application file for complete search history.

*Primary Examiner* — Kent L Bell

(57) ABSTRACT

A kiwifruit plant particularly distinguished by cylindrical fruit shape with a concave stylar end, pale yellow fruit flesh with red color radiating from the axial ovary, early fruit maturity and an average fruit weight of 90 to 94 grams is described.

9 Drawing Sheets

Genus and species: *Actinidia chinensis.*
Variety denomination: 'Yang's Golden Red No. 1'.

BACKGROUND OF THE INVENTION

The present invention relates to a new and distinct variety of *Actinidia chinensis* (kiwifruit) hereinafter referred to by the cultivar name 'Yang's Golden Red No. 1' or the 'new plant'. 'Yang's Golden Red No. 1' was selected from a population of seedlings derived from crossing two kiwifruit selections 'Hongyang' (U.S. Plant patent application Ser. No. 11/645,130—now abandoned), the female; and 'Male No. 13' (unpatented), the non-fruiting male; using controlled pollination in the course of a planned kiwifruit variety breeding program. The new plant was selected on 9 Sep. 2004 at Huaisi Town, Yangzhou, China.

The new plant has been asexually propagated by grafting in Huaisi Town, Yangzhou, China and the unique combination of characteristics of the new plant has been found to be reproducible and stable in successive generations of propagation. In order to obtain true-to-type clones of the initial plant, asexually propagated plants were obtained by grafting dormant buds from the original seedling onto *Actinidia deliciosa* rootstock.

Plant Variety Rights for 'Yang's Golden Red No. 1' were granted in China on 1 Nov. 2014 and assigned the grant number CNA20110642.7.

SUMMARY OF THE INVENTION

The following are the most outstanding and distinguishing characteristics of the new plant when grown under normal horticultural practices in Huaisi Town, Yangzhou, China:

1. Cylindrical fruit shape with concave stylar end
2. Pale yellow fruit flesh with red color radiating from the axial ovary 3. Early maturing fruit
4. Average fruit weight of 90 to 94 grams

DESCRIPTION OF THE PHOTOGRAPHS

The new plant is illustrated by the accompanying photographs which show in full color typical specimens of the plant habit, foliage, fruit and flowers of the new variety 'Yang's Golden Red No. 1'. The colors shown are as true as can be reasonably obtained by conventional photographic procedures. The photographs include plants approximately five years after grafting onto *Actinidia deliciosa* 'Hayward' (unpatented) rootstock in optimum conditions in Huaisi Town, Yangzhou, China.

DESCRIPTION OF THE NEW CULTIVAR

Figure 1:
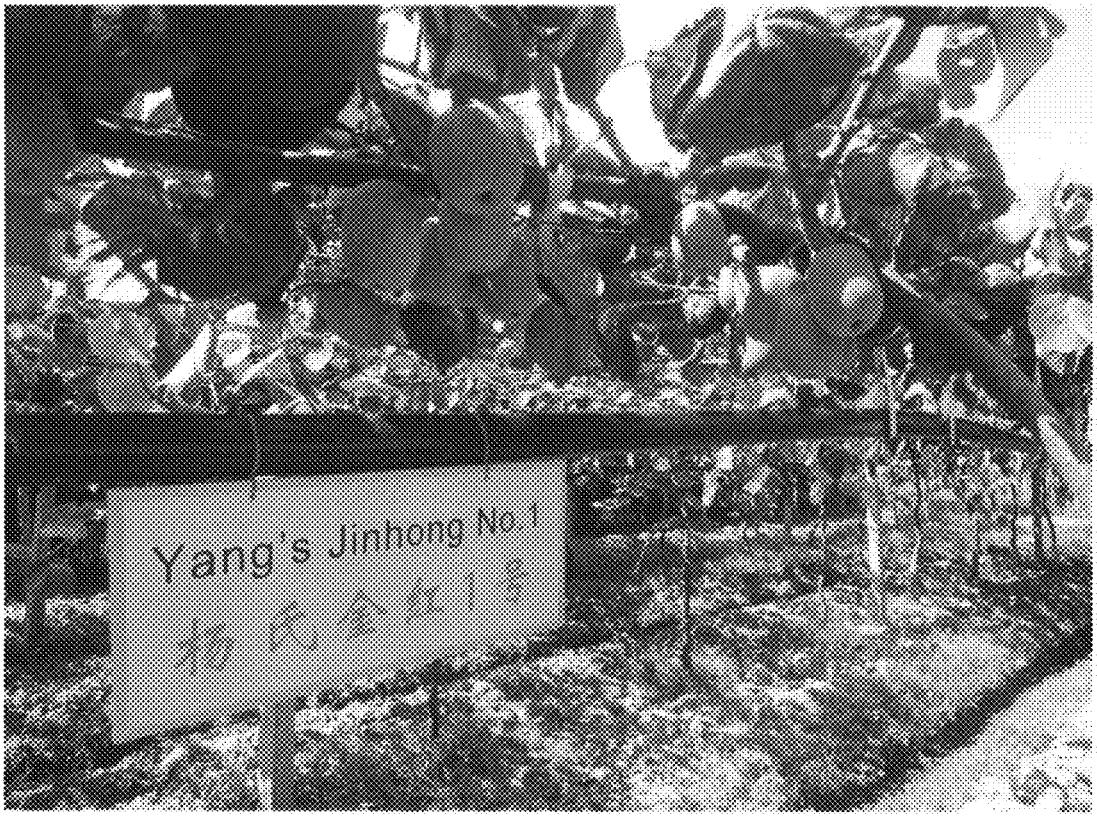
FIG. 1 shows typical fruit on the vine
Figure 2:
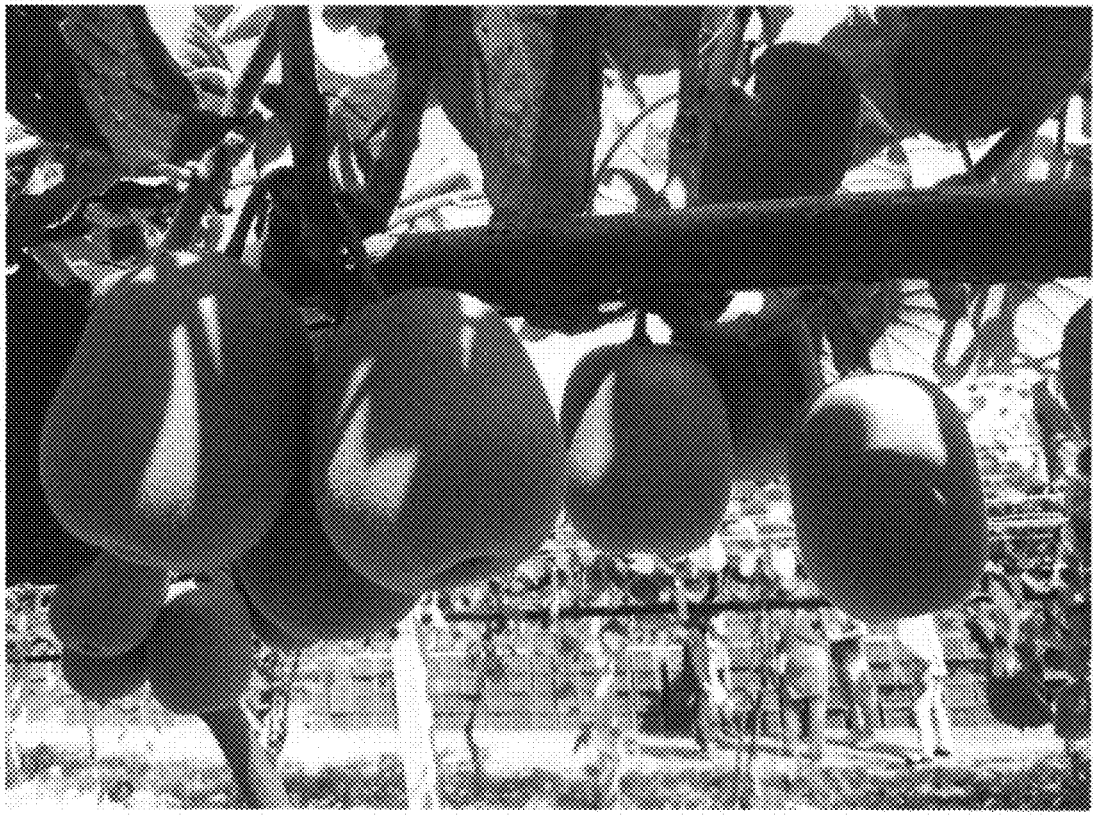
FIG. 2 shows a close up of typical fruit on the vine
Figure 3:
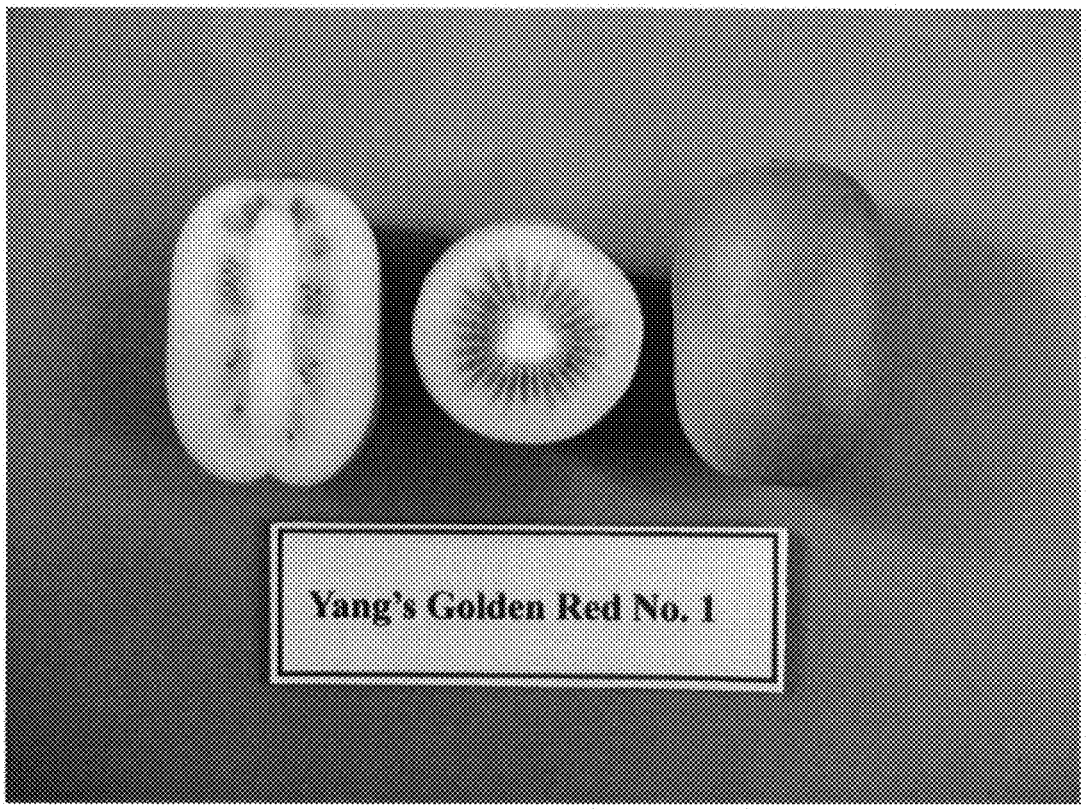
FIG. 3 shows fruit in longitudinal section and cross section in the studio
Figure 4:
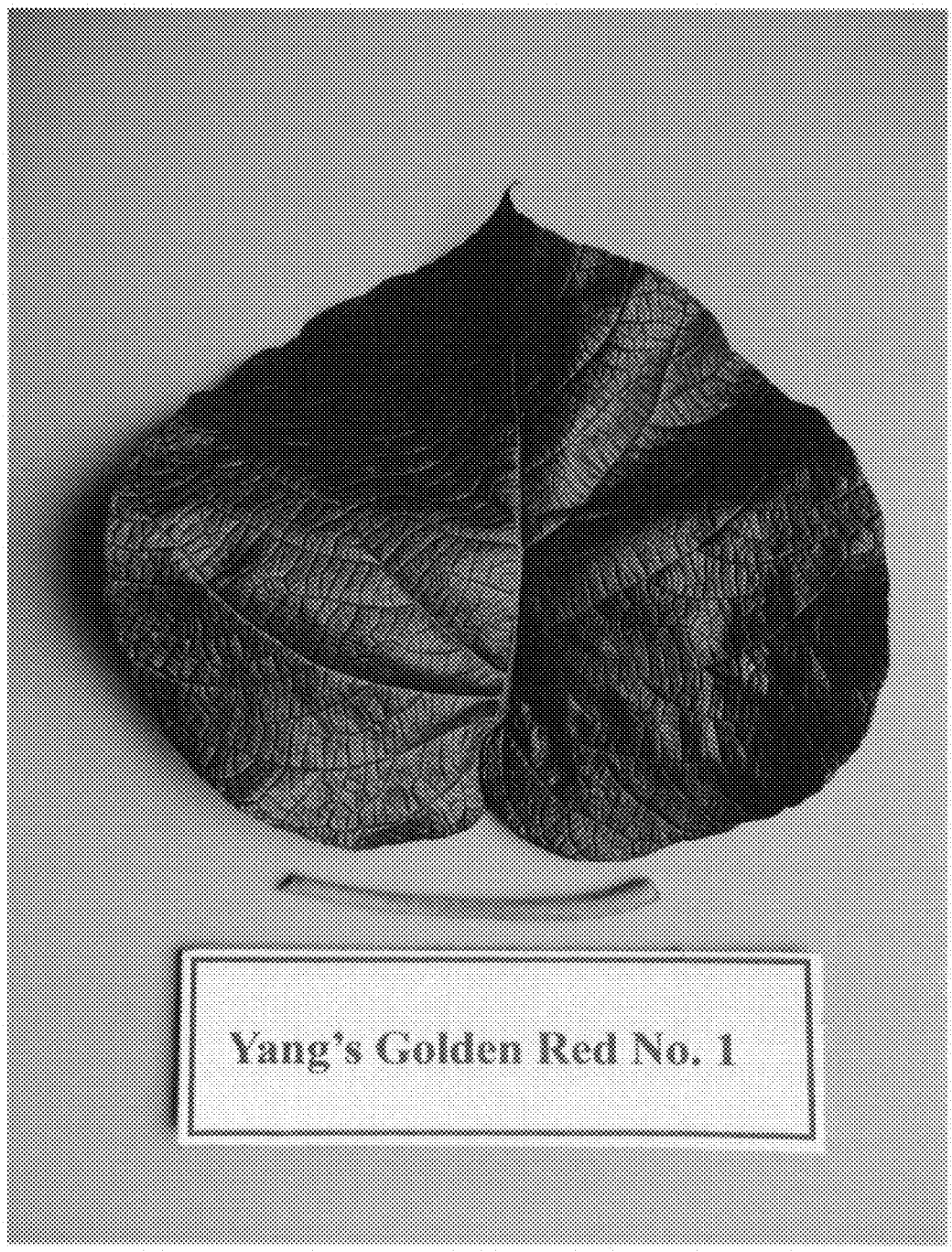
FIG. 4 shows upper surface of mature leaves in the studio
Figure 5:
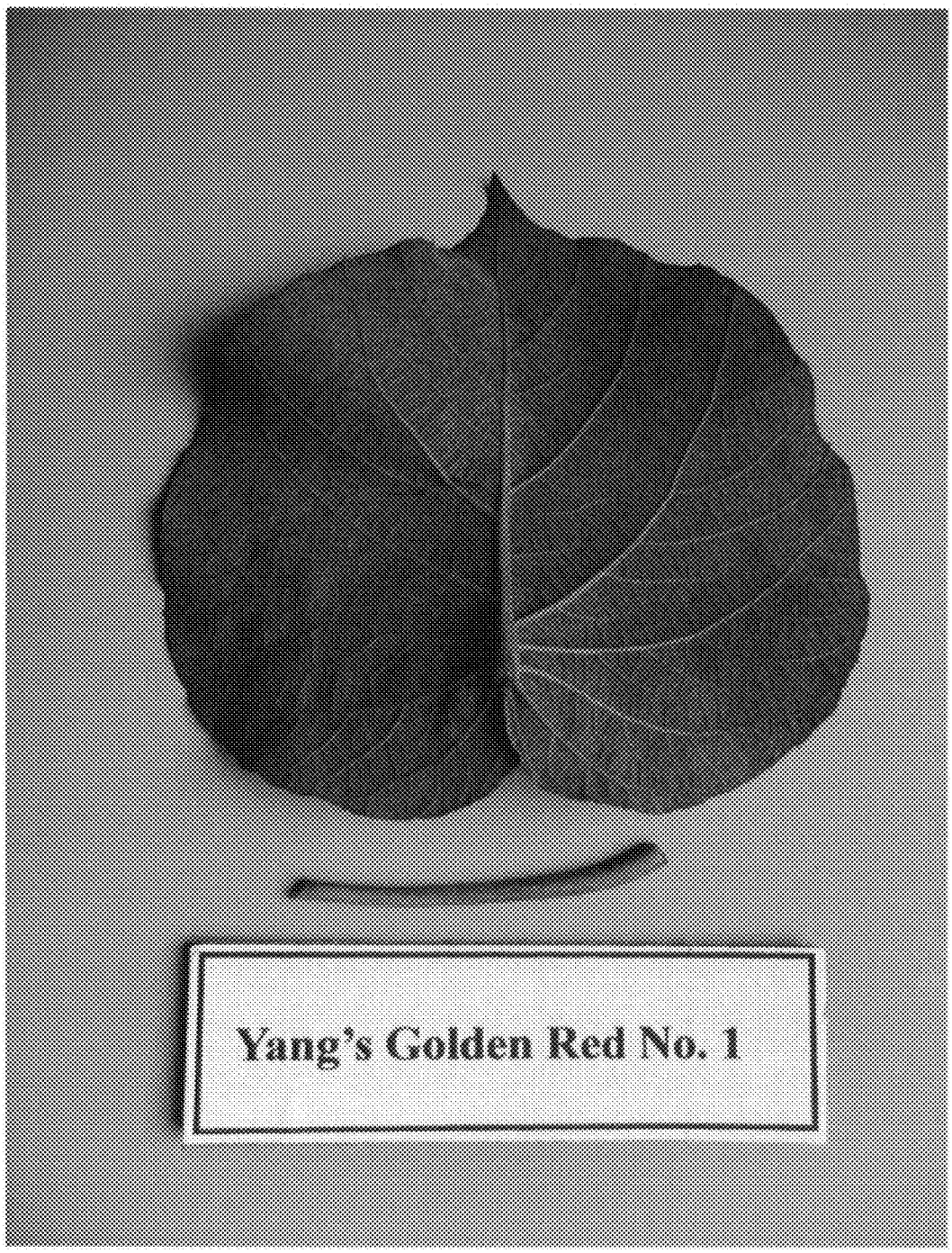
FIG. 5 shows lower surface of mature leaves in the studio
Figure 6:
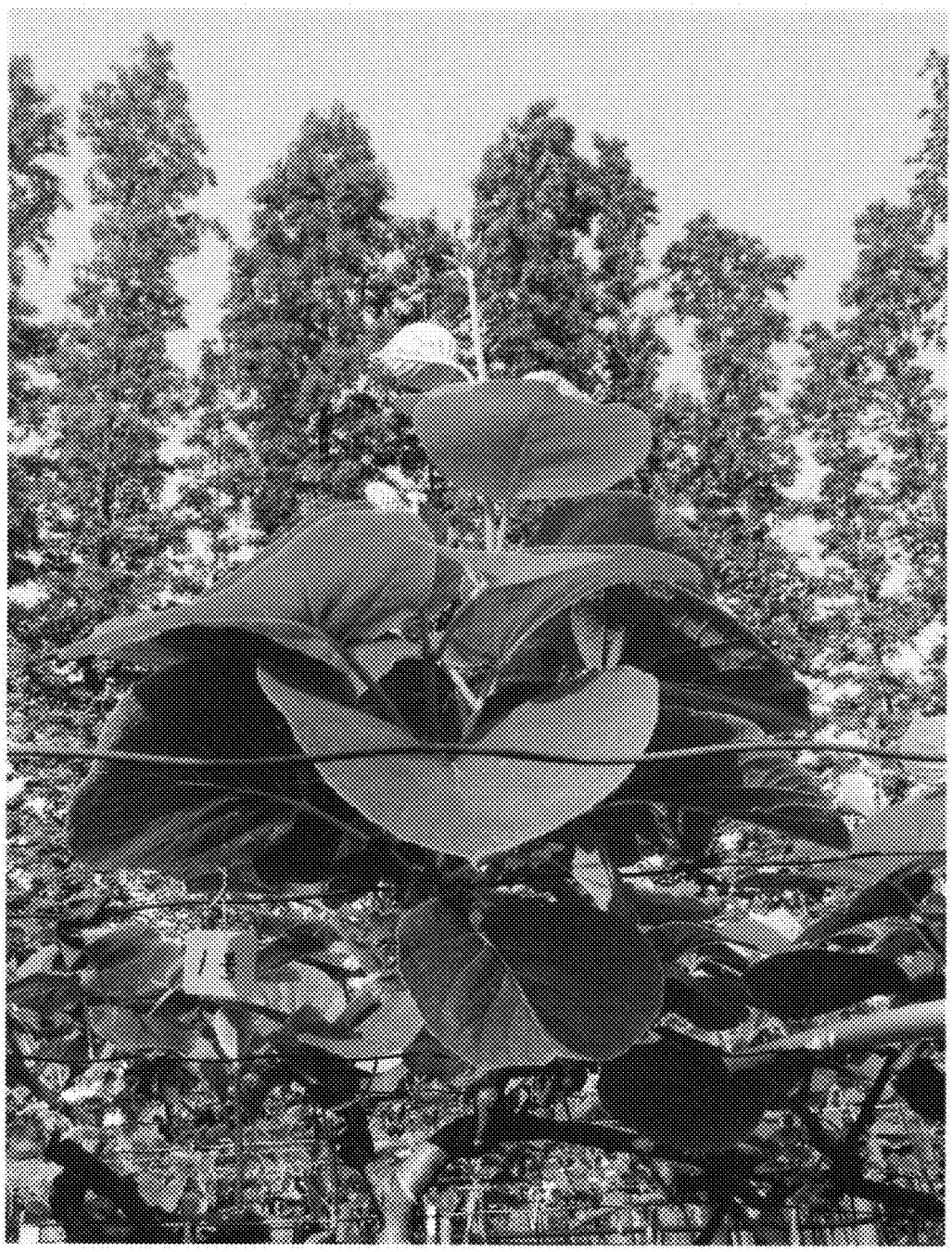
FIG. 6 shows young leaves and one year old shoots on the vine
Figure 7:
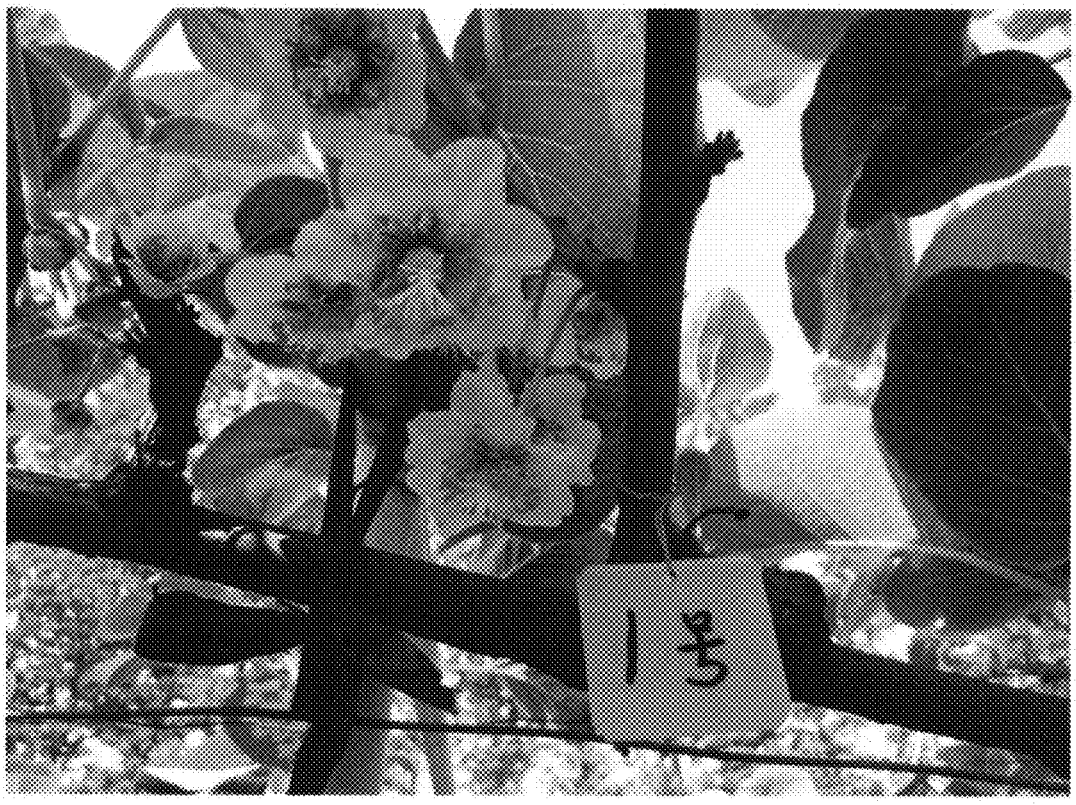
FIG. 7 shows flowers on the vine
Figure 8:
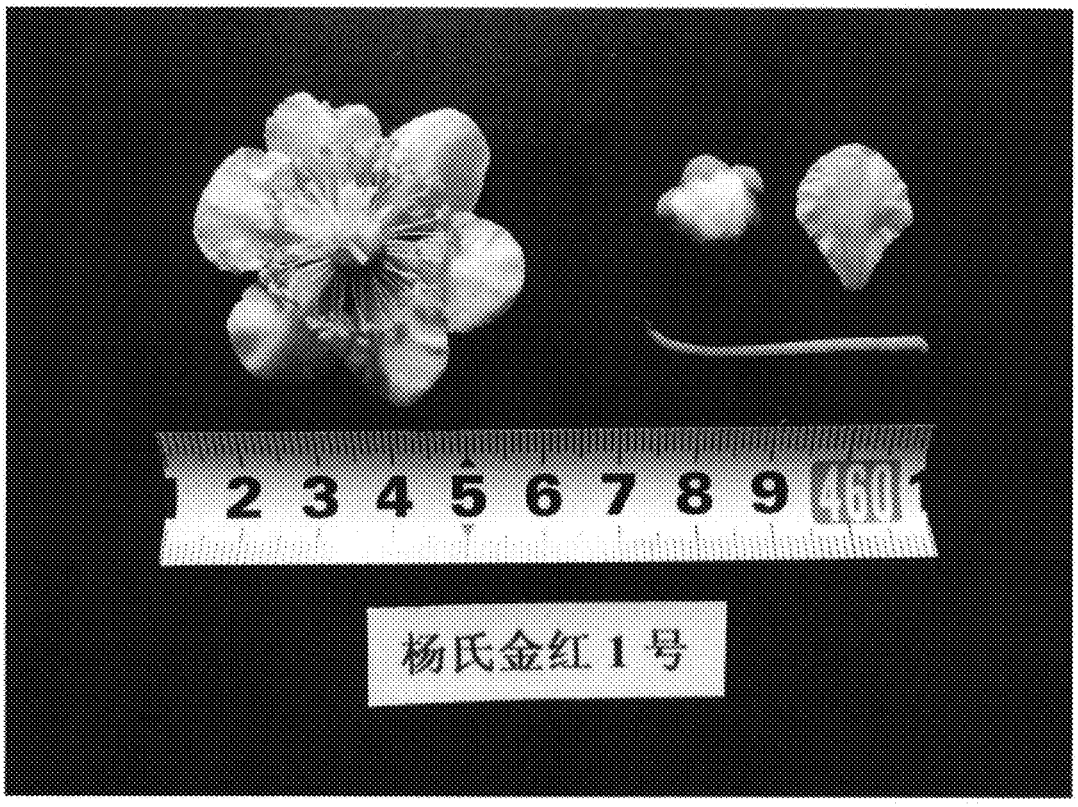
FIG. 8 shows typical flower, flower bud, petal and pedicel in the studio
Figure 9:
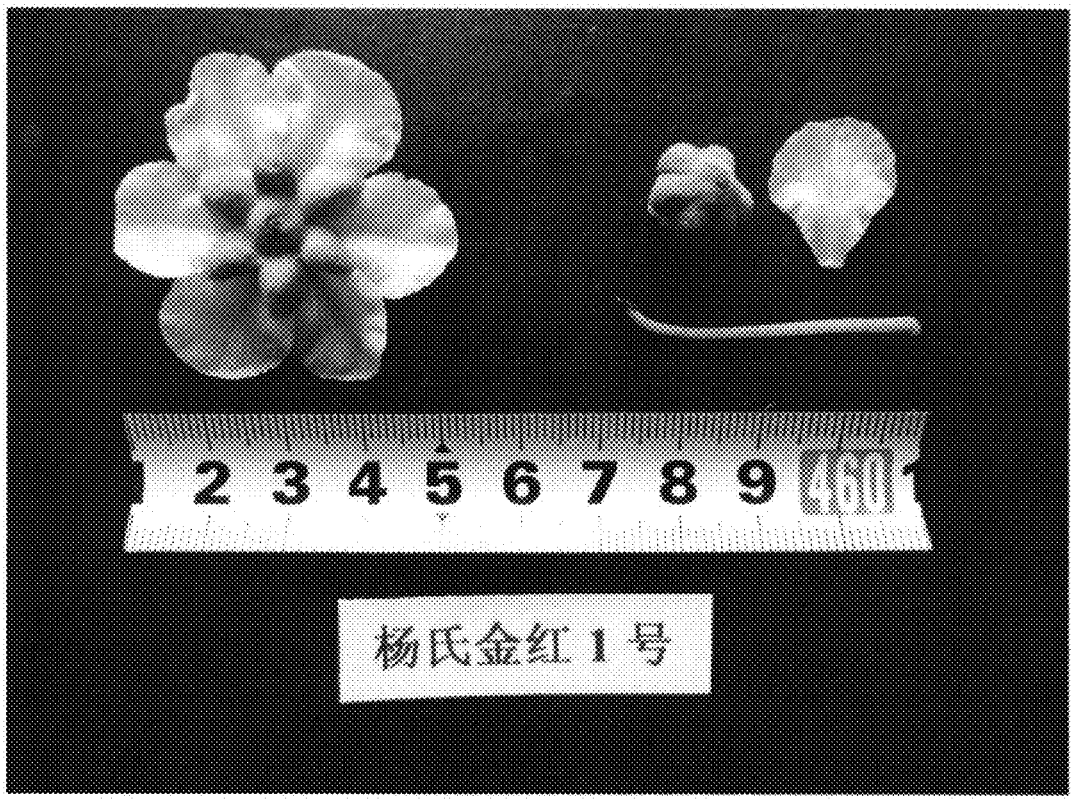
FIG. 9 shows typical flower, flower bud, petal and pedicel in the studio

The following detailed description sets forth the distinctive characteristics of 'Yang's Golden Red No. 1'. The following observations, measurements and values were made on five year old vines grafted onto *Actinidia deliciosa* 'Hayward' (unpatented) rootstock, and managed under standard orchard practice in Huaisi Town, Yangzhou, China.

Random measurements of each characteristic were obtained from a sample of 50 plants unless otherwise stated.

Horticultural terminology is used in accordance with UPOV guidelines for kiwi. All dimensions are in millimeters, and all weights are in grams (unless otherwise stated). Certain characteristics of this variety, such as growth and color, may change with changing environmental conditions (e.g., light, temperature and moisture), nutrient availability, rootstocks, or other factors. Color readings were taken in natural light. Color references are primarily to the Fourth edition, 2001 of The Colour Chart published by The Royal Horticultural Society, London (R.H.S.), except where general colours of ordinary significance are used.

DETAILED BOTANICAL DESCRIPTION

Classification:

*Family*.—Actindiaceae.

*Botanical name*.—*Actinidia chinensis*.

*Common name*.—Kiwifruit.

Parentage:

*Female parent*.—A kiwifruit selection 'Hongyang' (U.S. Plant patent application Ser. No. 11/645,130—now abandoned).

*Male parent*.—A kiwifruit selection 'Male No. 13' (unpatented).

Plant:

*Plant habit*.—Female plant of twining habit and medium vigour.

*Average plant size*.—Plants are grown on a standard pergola structure; each plant was pruned to occupy a canopy area of approximately 5 $m^2$ and height of 1.8 m.

*Trunk diameter*.—40 mm to 50 mm at 75 cm above the ground and 50 mm above the graft.

*Ploidy*.—Tetraploid.

*Propagation*.—Grafting of dormant buds onto rootstock.

Shoots:

*Texture of young shoots*.—Smooth.

*Colour of young shoots*.—Green, RHS 141C.

*Texture of mature shoots*.—Smooth with slightly raised lenticels.

*Colour of mature shoots*.—Brown, RHS 200D.

*Diameter of mature shoots*.—10 mm to 18 mm.

*Lenticels on shoots*.—Quantity/density: 6-10 per $cm^2$. Length: 1 mm to 13 mm. Shape: narrowly elliptical. Colour: greyed-white, RHS 156C.

Leaves:

*Quantity per one meter of mature shoot*.—10 to 15.

*Arrangement*.—Alternate.

*Length* (*mature leaf*).—133 mm to 152 mm.

*Width* (*mature leaf*).—118 mm to 136 mm.

*Shape*.—Cordate.

*Apex*.—Obtuse.

*Base*.—Cordate, overlapping.

*Margin*.—Finely serrate.

*Leaf spines*.—Approximately 1 mm in length.

*Texture*.—Upper surface: slightly puckered, non-pubescent. Lower surface: no pubescence.

*Colour*.—Young leaves, upper surface: green, RHS 138A. Young leaves, lower surface: near green, RHS 138B. Mature leaves, upper surface: green, RHS 137B. Mature leaves, lower surface: near green, RHS 138C.

*Venation*.—Pattern: reticulate. Colour, upper surface: near green, RHS 138A. Colour, lower surface: near green, RHS 138C.

*Petiole* (*leaf stem*).—Length: 120 mm to 140 mm. Diameter (cross section): 3.2 mm to 3.9 mm. Colour: near green, RHS 138A.

*Texture*.—Smooth, no pubescence.

Inflorescence

*Inflorescence type*.—One king flower with occasional 1-2 smaller side flowers.

*Natural flowering season*.—Full bloom during late April.

*Flowering duration*.—5-7 days.

*Flower number per square meter*.—70 to 100.

*Fragrance*.—Light.

*Longevity of viable flowers on the plant*.—5 to 6 days.

*Pedicel* (*stalk holding each flower*).—Strength: moderate. Length: 40 mm to 60 mm. Diameter: 1.5 mm to 1.8 mm. Colour: green, RHS 138C. Texture: sparsely pubescent.

*Flowers*.—Flower bud (diameter): 12 mm to 16 mm. Flower bud (length): 6 mm to 7 mm. Colour of bud: green, RHS 139C. Shape of bud: round to slightly elliptical. Diameter of individual flower: 30 mm to 45 mm. Arrangement of petals: overlapping.

*Petals*.—Quantity: 6 to 7. Length: 20 mm to 25 mm. Width: 15 mm to 17 mm. Shape: oblanceolate. Margin: undulate. Apex: retuse. Base: cordate. Type of colouration: Colour, primary when fully opened: white, 155C. Colour, base of petals and centre when fully opened: green white, 157C.

*Sepals*.—Quantity: 6 to 7. Length: 5 mm to 8 mm. Width: 4 mm to 7 mm. Shape: oblanceolate. Margin: entire. Apex: broadly acute. Base: rounded. Colour: green, RHS 138B. Texture: tomentose.

*Peduncles*.—Length: 38 mm to 45 mm. Diameter: 1.8 mm to 2.0 mm. Colour: green, RHS 138C. Texture: sparsely pubescent.

Reproductive organs:

*Styles*.—Quantity: 30 to 40. Attitude: semi erect. Colour: white, RHS 155C.

*Stamens*.—Quantity: 60 to 80.

*Anthers*.—Colour: orange, RHS 24A.

*Ovary*: (*king flower*).—Length: 8-9 mm. Shape: ellipsoid. Colour: white, RHS 155C. Texture: densely pubescent.

Fruit:

*Length*.—48 mm to 55 mm.

*Diameter*.—39 mm to 45 mm.

*Weight range*.—85 g to 100 g.

*Average weight*.—90 to 94 g.

*Skin*.—Texture: sparsely pubescent. Colour at harvest: yellow green, RHS 152C. Adherence to flesh: strong.

*Shape*.—Longitudinal: cylindrical. Cross section: circular. Stylar end: concave. Shoulder: squared.

*Calyx ring*.—Present. Expression: strong.

*Stalks*.—Length: 38 mm to 45 mm. Diameter: 2 mm to 3.1 mm. Texture on mature fruit: smooth. Colour on mature fruit: green, RHS 139C.

*Lenticels*.—Quantity: 30-40 per $cm^2$. Colour: yellow green, RHS 152C. Size: 1-2 mm (diameter).

*Pericarp*.—Outer colour, early: green, RHS 141C. Outer colour, mature: yellow green, RHS 152C. Inner colour, mature: green yellow, RHS 1D; colour moderately radiating around seeds red, RHS 43C.

*Core of fruit*.—Colour, mature: white, RHS 155C. Shape: transversely elliptical. Quantity of locules: 30 to 42. Quantity of Seeds: 40 to 50 per transverse slice through middle of fruit. Colour of seeds: greyed orange, RHS 165B. Size of seeds: approximately 1.8 mm long by 0.8 mm wide.

*Flavour*.—Taste: sweet. Dry matter at harvest: 17% to 19%. Dry matter at consumption: 19-22%. Brix level at harvest: 7%. Brix level at consumption: 17% to 20%.

*Storage*.—20 weeks at 1 degree Celsius.

*Overall fruit cropping per hectare*.—25 to 40 tons.

Rootstock: 'Yang's Golden Red No. 1' is commonly grown on *Actinidia deliciosa* seedling rootstock.

Vegetative bud break:

*Timing*.—Mid-March.

*Quantity of buds breaking*.—75% to 85%.

*Crop load*.—2.5 kg to 3 kg per square meter average.

*Leaf senescence*.—Late November.

Disease resistance: No observations made.

Insect resistance: No observations made.

Temperature tolerance: Tolerates low temperatures to approximately −5° C. without negative effects, tolerates high temperatures to approximately 35° C. without negative effects.

COMPARISON WITH PARENTAL AND KNOWN CULTIVARS

When compared to the female parent 'Hongyang' (U.S. Plant patent application Ser. No. 11/645,130—now abandoned); 'Yang's Golden Red No. 1' has a greater number of lenticels on the shoots, longer petioles, longer fruit stalks and a heavier average fruit weight.

When compared to the male parent 'Male No. 13' (unpatented) which is a non-fruiting male pollinator; 'Yang's Golden Red No. 1' has brown mature stems with elliptical lenticels, cordate leaves and bears fruit; whereas 'Chinensis Male No. 13' (unpatented) has dark grey mature stems with circular lenticels, widely ovate leaves and does not bear fruit.

When compared to the commercial variety 'Hort16A' (U.S. Plant Pat. No. 11,066); fruit of 'Yang's Golden Red No. 1' is cylindrical in shape with a concave stylar end, squared shoulder and has pale yellow flesh with red color radiating from the axial ovary; whereas fruit of 'Hort16A' (U.S. Pat. No. 11,066) is ovoid in shape with a strong pointed stylar end, rounded shoulder and has golden yellow flesh.

When compared to the commercial variety 'Yang's Golden Red No. 50' (U.S. Plant Pat. No. 26,450); 'Yang's Golden Red No. 1' has smaller leaves, fruit has a concave stylar end as opposed to a slightly blunt protruding stylar end, fruit matures 3-4 weeks earlier and has fewer seeds and a lower average weight.

I claim:

1. A new and distinct cultivar of kiwifruit plant as shown and described herein.

* * * * *